United States Patent
Steijns et al.

(10) Patent No.: US 8,329,759 B2
(45) Date of Patent: Dec. 11, 2012

(54) LONG TERM WEIGHT MAINTENANCE

(75) Inventors: Jan Steijns, Boekel (NL); Peter Zuurendonk, Leiden (NL); Bengt Herslöf, Stockholm (SE); Annika Viberg, Järfälla (SE)

(73) Assignee: DSM IP Assets B.V., Heerlen (NL)

( * ) Notice: Subject to any disclaimer, the term of this patent is extended or adjusted under 35 U.S.C. 154(b) by 937 days.

(21) Appl. No.: 12/158,001

(22) PCT Filed: Dec. 20, 2006

(86) PCT No.: PCT/SE2006/050599
§ 371 (c)(1),
(2), (4) Date: Oct. 14, 2008

(87) PCT Pub. No.: WO2007/075142
PCT Pub. Date: Jul. 5, 2007

(65) Prior Publication Data
US 2009/0209663 A1 Aug. 20, 2009

(30) Foreign Application Priority Data
Dec. 24, 2005 (SE) ..................... 0502919

(51) Int. Cl.
*A61K 47/44* (2006.01)
*A23D 7/06* (2006.01)
*A23K 1/18* (2006.01)

(52) U.S. Cl. ............. 514/783; 426/602; 426/2; 424/439

(58) Field of Classification Search ............. 514/783; 426/602, 2; 424/439
See application file for complete search history.

(56) References Cited

U.S. PATENT DOCUMENTS

| 6,517,883 B1 * | 2/2003 | Herslof et al. | 426/602 |
| 2007/0082025 A1 * | 4/2007 | Catani et al. | 424/439 |

FOREIGN PATENT DOCUMENTS

| WO | 99/02041 | 1/1999 |
| WO | 01/91587 | 12/2001 |
| WO | 2004/057982 | 7/2004 |
| WO | 2005/025322 | 3/2005 |

OTHER PUBLICATIONS

Mifflin, M.D. et al., "A New Predictive Equation for Resting Energy Expenditure in Healthy Individuals", Am J. Clin. Nutr., vol. 51, pp. 241-247, (1990).

(Continued)

*Primary Examiner* — Savitha Rao
(74) *Attorney, Agent, or Firm* — Nixon & Vanderhye P.C.

(57) ABSTRACT

This invention is in the field of weight maintenance, more in particular in the field of long term weight maintenance of humans. The invention relates to the use of a mixture of a triglyceride oil having a solid fat content at ambient to body temperature and an emulsifier for maintaining weight after weight loss. The invention also relates to the use of a mixture of a triglyceride oil having a solid fat content at ambient to body temperature and an emulsifier for obtaining a thermogenic effect. The invention also relates to the use of a mixture of a triglyceride oil having a solid fat content at ambient to body temperature and an emulsifier for increasing the energy expenditure such as resting energy expenditure.

5 Claims, 7 Drawing Sheets

```
week 1 week 2        week 7 week 8                    week 25 week 26
  △   ▽               △   ▽                            △     ▽
  └┬┘ └─────┬─────┘   └──────────┬──────────┘
  3 days    week 2-8                    week 8-26
  energy balance  very low energy diet    weight maintenance phase
  diet                                    with either placebo or Olibra
                                          yogurt
```

△  hunger, satiety hormones, questionnaires, blood samples

▽  standard parameters, energy expenditure

OTHER PUBLICATIONS

St-Onge, M-P et al., "Medium-Versus Long-Chain Triglycerides for 27 Days Increases Fat Oxidation and Energy Expenditure Without Resulting in Changes in Body Composition in Overweight Women", International Journal of Obesity, vol. 27, No. 1, pp. 95-102, (Jan. 2003).

St-Onge, M-P et al., "Medium Chain Triglyceride Consumption Increases Energy Expenditure Relative to Long Chain Triglyceride in Overweight Men"., Am. J. Clin. Nutr., vol. 75, No. 2, pp. 340S-341S, (2002).

International Search Report for PCT/SE2006/050599, mailed Mar. 29, 2007.

* cited by examiner

LONG TERM WEIGHT MAINTENANCE

This application is the U.S. national phase of International Application No. PCT/SE2006/050599, filed 19 Dec. 2006, which designated the U.S. and claims priority to Sweden Application No. 0502919-4, filed 24 Dec. 2005, the entire contents of each of which are hereby incorporated by reference.

FIELD OF THE INVENTION

This invention is in the field of weight maintenance, more in particular in the field of long term weight maintenance of humans.

BACKGROUND OF THE INVENTION

The increasing incidence of obesity is a recognized medical problem in developed countries. Obesity is a major factor for a number of diseases, including coronary heart diseases, hypertension, non-insulin dependent diabetes mellitus, pulmonary dysfunction, osteoarthritis and certain types of cancer. Obesity develops when the equilibrium between energy intake and energy expenditure shifts towards a positive energy balance.

Obesity can be classified as a mild (20-30% overweight), moderate (30-60% overweight) or a severe (>60% overweight) condition. Obesity is accompanied by a number of health hazards. It may impair both cardiac and pulmonary functions, perturb endocrine functions and cause emotional problems. Hypertension, impaired glucose tolerance and non-insulin dependant diabetes mellitus and hypercholesterolemia are more common conditions in overweight individuals than in individuals of normal weight. Obesity may therefore contribute to morbidity and mortality in individuals suffering from e.g. hypertension, stroke, diabetes type II, some types of cancer, gallbladder disease and ischemic heart disease. Moderate and severe cases of obesity are known to increase mortality. Colon and rectal cancer are diseases which frequently appear in obese men, and obese women often suffer from endometrial or gallbladder cancer. Furthermore, it is realized that an increase in overweight almost consequently leads to a rise in psychic and social problems.

Treatment of obesity is beneficial in that weight loss reduces the risk for mortality and morbidity. Even modest weight loss already leads to beneficial health effects. Body weight loss is known to be achieved by reducing energy intake and/or increasing energy expenditure, or promoting fat oxidation. (Clinical guidelines on the identification, evaluation and treatment of overweight and obesity in adults—The evidence report. NIH. Obes. Res. 1998; 6 (suppl): 51S-209S).

A first effective method for loosing weight is the reduction of energy intake, i.e. food intake. This is essentially possible only through a dietary treatment as malabsorption of food cannot be obtained safely either through medication or surgery. The dietary treatment must consist of a weight reducing diet as well as a maintaining diet. After a satisfactory weight loss, the energy supply must slowly be increased until the weight has stabilized on a supply of food which is nutritious and acceptable for the patient. The importance of a long-term diet is seen from the fact that only 10-20% of the patients are able to maintain their obtained reduced weight.

Secondly, increase in physical activity will lead to increased energy expenditure and consequently contribute to a negative energy balance. However, in order to obtain a significant weight loss, hours of daily physical activity are needed. Physical activity alone therefore plays a minor role in the treatment of obesity, although it is a very important supplement to other kinds of treatment. Also, physical activity can contribute to diminution of the decrease in energy expenditure which follows a dietary treatment comprising an energy restriction.

Drugs can be used in the treatment of obesity, either alone or in combination with a dietary treatment and/or increased physical activity. The drugs used in the treatment of obesity are mostly appetite reducing drugs and/or thermogenic drugs. The appetite-reducing drugs exert their effect primarily by decreasing energy intake. The reduction in food consumption is a consequence of the drug action on the brain transmitter systems that are involved in the appetite regulation. The action of these drugs is supposed to be mediated through the hypothalamus at various sites. The action can be exerted through the adrenergic, the dopaminergic or the serotonergic pathway or a combination thereof. Whichever system is involved, the final result is a stimulation of the satiety centre and eventually a simultaneous decrease in activity of the feeding centre which results in a depressed appetite. Examples of known appetite-reducing agents are e.g. ephedrine, phenylpropanolamine, amphetamines and fenfluramine.

Thermogenic drugs in the treatment of obesity are now generally accepted to possess a potential therapeutic value, and in the recent years there has been a growing interest in the search for new thermogenic compounds. The interest is primarily related to the well-accepted suggestion that obesity might be genetically determined. The genetic defect responsible for the possible development of obesity relates to a thermogenic defect (i.e. a defect in the metabolic system) of the obese person (Dulloo, A. and D. S. Miller (1989) Nutrition 5: 7-9). Although the nature of the thermogenic defect is not fully clarified, there is compelling evidence that points to a defective reactivity of the sympatoadrenal system (Astrup, A. V. (1989). Nutrition 5: 703). Dulloo & Miller (1989) Nutrition 5: 7-9) suggest that the thermogenic defect of the obese persons relates to a reduced release of norepinephrine rather than to an insensitivity to the neurotransmitter. Drugs which mimic the activity of the sympathetic nervous system and increase metabolic rate therefore offer considerable therapeutic potential for the treatment of obesity.

As used herein, the term thermogenic is meant to mean the production of heat, especially by physiological processes. A thermogenic drug is therewith a drug capable of inducing the physiologic production of heat in the human or animal body and/or fat oxidation.

Whereas a number of successful weight reduction methods are available, long term weight maintenance remains a problem. Elfhag and Rossner (Obesity Reviews (2005) 6, 67-85) reviewed a number of factors associated with successful weight maintenance after weight loss and concluded that an internal motivation to loose weight, social support, better coping strategies and ability to handle life stress, self-efficacy, autonomy, assuming responsibility in life and overall psychological strength and stability were the dominant factors that determined whether a patient would succeed to maintain his weight after an intentional weight loss. Patients are encourages to find their very unique personal solutions and inner capacities.

The reason why it is so difficult to maintain the desired weight is often contributed to the fact that in human subjects, basal metabolic rate (BMR) decreases during weight reduction, which is probably due to loss of fat free mass, fat mass and lower sympathetic nervous system activity. This effect may be particularly important in obese patients. A meta analysis of basal metabolic rate showed that formerly obese patients had a significant 3-5% lower BMR and a five-fold higher risk of having a low BMR than the never-obese (Astrup et al., (1999) Am. J. Clin. Nutr. 55:14-21).

Pharmaceutical research has addressed this problem and it was recently found that the drug Sibutramine not only provided an effect on appetite reduction but also could successfully increase energy expenditure after intentional weight loss. With a higher dose of Sibutramine, an acute thermogenic effect was observed in normal weight male subjects (Hansen et al. (1998) Am. J. Clin. Nutr. 68: 1180-1186) whereas a lower chronic dose of Sibutramine did not raise the energy expenditure but did have an effect of disinhibiting the normal reduction in energy expenditure seen with decreasing energy intake and weight loss (Hansen et al., (1999) Int. J. Obes. 23: 1016-1024).

Sibutramine is a serotonin and noradrenaline re-uptake inhibitor, and is recommended by the National Institute of Clinical Excellence (NICE) for the treatment of obesity in patients with a BMI of over 30 kg/m2 or the presence of an obesity-related disease and a BMI of over 27 kg/m2 (NICE. (2001) Guidance of the use of Sibutramine for the Treatment of Obesity in Adults. Technology Appraisal Guidance—No 31. National Institute for Clinical Excellence, London).

In a recent European trial (James et al., (2000) Lancet, 356: 2119-2125), following a 6-month run-in period on sibutramine, patients who achieved a 5% reduction in weight were randomized to either continue with sibutramine or receive placebo. At 18 months, 69% of patients on sibutramine compared with 42% of controls retained this modest 5% reduction.

However, Sibutramine may cause an increase in blood pressure and pulse (acting as a sympathomimetic) and is therefore unsuitable for hypertensive patients. In normotensive patients, treatment with sibutramine may achieve moderate weight loss for a limited period at least. Sibutramin also suffers from a number of side effects that include constipation, dry mouth, elevated blood pressure, headache, increased heart rate and sleeplessness (http://www.meridia.net/index.cfm?act=consumer_safety).

A number of other drugs have been suggested to address the problem of weight maintenance after weight loss. The drugs fenfluramine and dexfenfluramine, which acted through stimulation of 5-HT secretion as well as inhibition of 5-HT re-uptake, were withdrawn following the discovery of an association with their use and cardiac valve abnormalities (Connolly et al., (1997) New England Journal of Medicine, 337: 581-588)

Orlistat acts locally in the gut by binding to gastrointestinal lipases to inhibit fat absorption. Patients who take Orlistat with or 1 h after meals excrete approximately one-third of their ingested dietary fat in their stools, thereby reducing calorie intake. Consequently, they may have flatulence and offensive stools after a fatty meal. Trials show that Orlistat can also achieve mild weight loss of 9% at 1 years compared with 5% of placebo and may slow the regain of weight for a second year of use (Yanovski & Yanovski (2002), New England Journal of Medicine, 346: 591-602). However, Orlistat is only licensed for 2 years, and is less effective by the second year.

In conclusion, there remains a need for thermogenically active compositions that can enhance the energy expenditure of a human body in order to help maintain weight after weight loss. In particular, pharmacologically active compositions that do not suffer from the above mentioned side effects would be beneficial.

SUMMARY OF THE INVENTION

Surprisingly, it was found that a mixture of a triglyceride oil having a solid fat content at ambient to body temperature and an emulsifier, preferably a food emulsifier can effectively be used to maintain weight after weight reduction. Such compositions appear to increase the resting energy expenditure after weight loss, contribute to a loss of fat free mass and to increase fat free mass.

The invention therefore relates to the use of a mixture comprising a triglyceride oil having a solid fat content at ambient to body temperature and an emulsifier for the preparation of a pharmacologically active composition for increasing energy expenditure such as resting energy expenditure.

The invention also relates to the use of a mixture essentially consisting of a triglyceride oil having a solid fat content at ambient to body temperature and an emulsifier for the preparation of a pharmacologically active composition for increasing energy expenditure such as resting energy expenditure. Such a mixture may of course additionally comprise colorants, antioxidants etc.

The invention also relates to the use of a mixture of a triglyceride oil having a solid fat content at ambient to body temperature and an emulsifier for the preparation of a pharmacologically active composition for obtaining a thermogenic effect.

Such use is particularly advantageous for maintaining weight after a period of weight loss.

The invention therefore also relates to the use of a mixture of a triglyceride oil having a solid fat content at ambient to body temperature and an emulsifier for the preparation of a pharmacologically active composition for maintaining weight after weight loss.

DETAILED DESCRIPTION OF THE INVENTION

The terms "weight maintenance" or "maintaining weight loss" imply keeping an approximate weight loss result that may have been accomplished by treatment interventions or by one's own efforts, for a period of at least 18 weeks. More in particular, the term "weight loss" refers to achieving a weight loss of at least 2% of initial or baseline body weight, such as 3, 4, 5, 7, 10 or even 15%. A weight loss may be considered maintained when weight regain, 18 weeks after the end of a period of weight loss, as a % of weight loss, does not exceed 35%, such as 30, 25, 20 or even 15% or less.

Alternatively, weight loss may also be expressed as loosing 2 or more body mass index (BMI) points whereas weight may be considered maintained when the regain of BMI as a percentage of lost BMI is less than 35%, such as 30, 25, 20 or even 15% or less, 18 weeks after the end of a period of weight loss.

The mixtures that may be used in the invention are advantageously oil in water emulsions. In this application, the term "Oil-in-water emulsions" refers to liquid oil dispersions as well as to solid fat dispersions, which are suspensions. The amount of triglyceride oils (wt %) may vary depending on the envisaged application and the nature and characteristics of the triglyceride oil as is taught herein. It can be envisaged that a composition according to the invention contains 5, 10, 15, 20, 30, 40, or even 60 or more wt % of triglyceride oils up to maximum dispersability, i.e. when there is still a water continues phase.

With the phrase "having a solid fat content at ambient to body temperature" it is meant that there should be a solid fat content in the whole interval between ambient and body temperature. The meaning of "a solid fat content" is known to the skilled person and may be determined using standard methodology, as for instance is provided at www.minispec.com/applications/solid_fat_content.html. Expressed in another way, the term means that there should be at least a residual and detectable solid fat content at body temperature. Residual and detectable solid fat contents may be in the order of more than 0.1%, such as 0.5%, 1%, 2%, 3%, 5%, 10% or more. Solid fat content may be determined by Benchtop NMR using ISO 8292 or IUPAC 2.150 methods. These methods yield a melting curve from which it can be easily determined whether a given triglyceride oil has a solid fat content in the range of ambient to body temperature.

Ambient temperature is used to indicate approximate room temperature being the temperature wherein the composition is used according to the invention. Usually this is approximately 20° C., such as 18, 19, 20, 21 or 22° C.

Body temperature differs slightly from species to species; herein this term is used to indicate the body temperature of the human individual to be treated. Usually this is approximately 37° C., such as 36, 36.5, 37, 37.5 38, 38.5 or 39° C.

The invention is particularly useful for maintaining a weight loss in overweight or obese individuals. For practical purposes, it is generally agreed that overweight is present if the body weight exceeds the "desirable weight", whereas obesity is present if the body weight is 20% or more above the "desirable weight". Desirable weights for humans can be defined according to Metropolitan Height and Weight Tables as the midpoint of the range of the medium-frame individuals.

The term "Triglyceride" as used herein refers to triacylglycerol, which is glycerol esterified to three fatty acids.

The triglyceride oils of said mixtures or oil in water emulsions can be any triglyceride material having a solid fat content at ambient to body temperature. The triglyceride oils are defined by the percentage of solid fat content, determined by NMR serial measurements as described in IUPAC method no. 2.150, 7th edition.

The triglyceride oils are preferably confectionery fats, such as palm oil, cocoa butter or other. Further examples of suitable triglyceride oils are illipe butter, shea butter, kokum butter, sal butter or other natural oils or fractions thereof with a similar solid fat content or melting range. Other examples of such oils are hydrogenated or partly hydrogenated soybean oil, rapeseed oil, cotton oil and sunflower oil or fractions thereof. The triglyceride oils may also be synthetic or semi-synthetic.

The term "confectionary fat" refers to special fats for confectionary applications and is known in the art. Cacao butter is the best known representative of this group, confectionary fats are also often referred to as cacao butter alternatives or cacao butter equivalents, sometimes also as cacao butter replacers or cacao butter substitutes.

The term synthetic or semi-synthetic refers to substances that are not entirely natural and/or obtained by chemical synthesis.

The invention especially refers to the use of compositions wherein the triglyceride oils comprise a fraction of palm oil. This fraction of palm oil may be obtained from commercial palm oil, which may be fractionated to specific mixtures of suitable triglycerides, based on the combination of mainly palmitic, oleic, linoleic and stearic esters of glycerol, respectively.

Preferred fatty acids for use in the invention are therefore selected from the group consisting of palmitic acid, oleic acid, linoleic acid and stearic acid. Even more preferred compositions comprise at least two fatty acids selected from the group consisting of palmitic acid, oleic acid, linoleic acid and stearic acid. Particularly good results were achieved when 20-80%, such as 30-70% of fatty acids were used selected from the group consisting of palmitic and stearic acid, and 80-20%, such as 70-30% fatty acids selected from the group consisting of oleic and linoleic acid. It should be noted that these amounts do not necessarily have to add up to 100%, i.e. they do not necessarily exclude the presence of additional fatty acids such as lauric acid.

The triglyceride oils may contain at least 90% by weight of triglycerides, such as more than 95% by weight. Also, the content of triglycerides in the palm oil fraction may be 99% or more by weight. The purity can be checked by conventional chromatographic methods, such as thin-layer chromatography or high-performance liquid chromatography. It is preferred that the triglyceride oils utilised in the emulsion are pure and free from unwanted contaminants when used for pharmacological purposes Any emulsifier may be used in the invention; however, food emulsifiers are preferred. Food emulsifiers are emulsifiers commonly used in food applications and are generally esters composed of a hydrophilic and a lipophilic part. In general, the lipophilic part comprises stearic, palmitic, oleic, or linoleic acid or a combination of said fatty acids. The hydrophilic part generally comprises hydroxyl, carboxyl, or oxyethylene groups.

Examples of families of food-grade emulsifiers are lecithins, mono- and diglycerides, propylene glycol monoesters, lactylated esters, polyglycerol esters, sorbitan esters, ethoxylated esters, succinylated esters, fruit acid esters, acetylated mono- and diglycerides, phosphated mono- and diglycerides and sucrose esters. The emulsion of the triglyceride oils can also be obtained when the oils are mixed with suitable foods or food products, making use of the inherent emulsification properties of said foods or food products. Food emulsifiers according to the invention may be able to emulsify more than 20% by weight of the triglyceride oils, preferably more than 40% by weight, giving an emulsion which is still liquid in order to facilitate the processing of a food product in which the emulsion may be incorporated.

A preferred emulsifier of the invention is lecithin, for instance produced from egg yolk, milk, soybean oil, sunflower oil, and rapeseed oil, which consists of a mixture of mainly phospholipids, such as phosphatidylcholine and phosphatidylethanolamine. Lecithin refers in this context to crude mixtures of said phospholipids which are obtained on degumming of the starting materials, and which are commercially available as food emulsifiers.

A particularly preferred emulsifier is a galactolipid based emulsifier. Galactolipids belong to the group of glycolipids, well known constituents of plant cell membranes. The most important classes of these contain one to four sugars linked glycosidically to diacylglycerol. The two most abundant classes contain one and two galactose units, respectively, and the commonly used nomenclature and abbreviations of these are mono- and digalactosyldiglyceride (MGDG and DGDG), sometimes referred to as galactolipids. Galactolipids, primarily DGDG and DGDG-rich materials, have been investigated and found to be a surface active material of interest in industrial applications such as food, cosmetics, and pharmaceutical products. Galactolipid emulsifiers are described in WO 95/20943 and WO 97/11141. Preferred sources for the galactolipid emulsifiers are cereals and grains, particularly oats.

A preferred aspect of the invention is the use of a composition wherein the triglyceride oils of the invention are combined with palm kernel oil or coconut oil.

Particularly good results were obtained when a fractionated oat oil was used as a galactolipid based emulsifier. The invention therefore also relates to the use of a composition wherein the galactolipid based emulsifier was a fractionated oat oil.

Oil-in-water emulsions may be prepared by using the emulsifier either alone or in combination with other amphiphilic compounds, such as co-surfactants. The oil-in-water emulsion may also comprise optional additives known in the art for improving different aspects of the composition, such as flavouring agents, sweeteners, colorants, thickening agents, preservatives, antioxidants, etc.

Oil-in-water emulsions may be prepared by conventional methods. For example, a 30 wt % emulsion of a triglyceride oil in water is prepared by adding the emulsifier to the liquid triglyceride. The continuous phase may be pure water or an aqueous solution containing water-soluble additives such as isotonic agents, sweeteners, flavours, and preservatives. If necessary, the pH of the aqueous phase is then adjusted. The oil phase as well as the aqueous phase is preheated and then the oil phase is added to the aqueous phase under high-shear mixing. The pre-emulsion may then be subjected to high-pressure homogenisation.

The compositions described herein may be administered in enteric or oral doses in order to obtain the thermogenic effect and/or the effect of weight maintenance after weight loss. Preferably, the compositions are administered in the form of a food substance.

Therefore, the mixture comprising the triglyceride oils plus the emulsifier may be added to solid or semi-solid foods, which then become naturally emulsified to an oil-in-water emulsion on exposure to the fluids of the gastrointestinal tract. The mixture may also contain oil-soluble additives such as antioxidants and flavours. The mixture may also be made into a ready-prepared emulsion which can be added to liquid or semi-liquid foods and drinks.

The invention particularly refers to a food composition wherein the mixture of triglyceride oils and emulsifier of the emulsion comprises 80-99% by weight of triglycerides and 1-20% by weight of emulsifier.

It should be emphasized that the emulsifying capacity of the emulsifier depends on the nature or properties of the emulsifier. The fractionated oat oil mentioned above can without further purification be used as an emulsifier in an amount of 1-20% by weight of the total composition for preparing oil-in-water emulsions of 5-60% by weight of triglycerides. The galactolipid emulsifier of WO 95/20943 should be used in 0.1-5.0% by weight of the total composition for preparing oil-in-water emulsions of 5-80% by weight of triglycerides.

The mixture can be used in formulation of dairy products, such as yogurt, ice cream, margarines, spreads, salad oils and dressings, processed meat products, confectionery, fillings, sauces, soups, fruit drinks, desserts, baby foods, but also nutritional and pharmaceutical supplements. Especially the oily mixture can be used in solid or semi-solid foods such as chocolates, other candies, baked goods and any other appropriate foods.

The invention also refers to the use of a dairy product comprising 1-30% by weight, preferably 2-15% by weight of the oil-in water emulsion. A preferred dairy product, such as a yogurt, may comprise 4-10% by weight of an emulsion of a triglyceride fraction of palm oil and fractionated oat oil.

In order to obtain the desired effect of weight maintenance, a 40 wt % emulsion may be taken in an amount of 1-200 ml per serving or meal, alternatively 5-100 ml or 10-30 ml. The oil component alone, that is the oily mixture, may be used in proportionally smaller quantities.

The invention also refers to the use of oil-in-water emulsion of triglyceride oils having a solid fat content at ambient to body temperature and an emulsifier for the preparation of a pharmacologically active composition for increasing energy expenditure, such as resting energy expenditure. This is particularly useful after a period of intentional weight loss.

When used in a pharmaceutical composition such a composition may in addition to the oil in-water emulsion comprise a therapeutically active component other than the components according to the invention. Therapeutically active components that may be added include vitamins, minerals and ethical drugs.

In the following Examples and Tests different lipids and emulsifiers have been formulated into mixtures and emulsions and tested as to effect on weight maintenance after weight loss. The following fats or oils have been used: Fractionated palm oil (CPL-Palm oil, LTP Lipid Technologies Provider AB, Karlshamn, Sweden) obtained by fractionation of Akofrite (trade name for a palm oil from Karlshamns AB, Karlshamn, Sweden.

As emulsifiers have been used Fractionated oat oil (Scotia LipidTeknik, Stockholm, Sweden) comprising about 20% DGDG, and prepared from oats in-accordance with WO 97/11141; Galactolipids (CPL-Galactolipids, Scotia LipidTeknik, Stockholm, Sweden) comprising about 60% DGDG, and prepared from oats in accordance with WO 95/20943.

The Fractionated palm oil used may have the following fatty acid composition as determined by means of gas-liquid chromatography after alkaline methanolysis: 40-45 wt % palmitic acid, 38-42 wt % oleic acid, 8-10 wt % linoleic acid, and 4-5 wt % stearic acid, the remainder being selected from the group consisting of lauric acid, myristic acid, arachidic acid and palmitoleic acid.

The Fractionated palm oil may have a triglyceride (TG) content of 99.8-100.0 wt %, a solid fat content at 20 and 35° C. (N and N35) of 31 and 6, respectively.

When the above described compositions were used as a food supplement for human individuals after a period of weight loss, it was observed that the resting energy expenditure of the individuals receiving a composition according to the invention (test individuals) was significantly higher than in those individuals that did not receive any of the compositions (control individuals). Also, the fat free mass of the test individuals was significantly higher whereas the fat mass was lower (table 5 and FIGS. 6 and 7).

Without wanting to be bound by theory, the observed effects of Olibra may be the result of the "ileal brake" mechanism, i.e. the inhibition of upper gastrointestinal functions elicited by the presence of unabsorbed nutrients in the ileum (Spiller et al, 1984). The "ileal brake" appears to be related to the release of one or more satiety hormones from the distal intestine (Aponte et al, 1985; Jin et al, 1993). It now also appears to play a role in the regulation of energy expenditure.

EXAMPLES

Example 1

Olibra Emulsion

Figure 1:
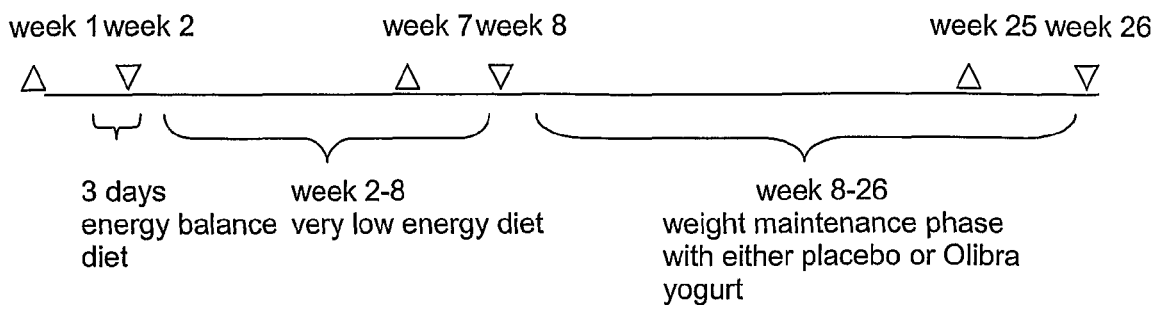
FIG. 1 is a schematic representation of the study design

Preparation of 40 wt % emulsions with Fractionated palm oil (batch size 300 g).

| Ingredients | wt % |
| --- | --- |
| Water | 58.0 |
| Fractionated palm oil | 40.0 |
| Fractionated oat oil | 2.0 |

The palm oil is melted at 50° C. and mixed with the fractionated oat oil. The oil phase and the water are preheated to 65-70° C. and then the oil phase is added to the water under high-shear mixing at 15,000 rpm for 4 min. The pre-emulsion is then divided into two parts; one part is homogenized at 400 bar, the other part at 800 bar, both for 6 cycles at 60° C. (Rannie homogenizer, Model Mini-Lab 8.30 H, APV Rannie, Denmark).

Both parts of the preparation result in emulsions with a similar cream-like consistency. The average particle size (Z average) is in both cases around 480 nm (Zetasizer 4, Malvern Instruments, UK).

An emulsion prepared as above (herein after called Olibra, and marketed by LTP Lipid Technologies Provider AB, Karlshamn, Sweden) can be stored at 2-8° C. until being used as an ingredient in the production of a product. The Olibra emulsion may be used as an ingredient in the manufacturing of a yogurt product.

Example 2

Other Oil in Water Preparations

Emulsion A

| Ingredients | wt % |
| --- | --- |
| Water | 58.0 |
| Fractionated palm oil | 40.0 |
| Galactolipids | 2.0 |

The palm oil is melted at 50° C. and mixed with the galactolipids. The oil phase and the water are preheated to 65-70° C. and then the oil phase is added to the water under high shear mixing at 15,000 rpm for 4 min. The pre-emulsion is homogenized at 800 bar, for 6 cycles at 60° C. (Rannie homogenizer, Model Mini-Lab 8.30 H, APV Rannie, Denmark). This results in an emulsion with a creamy consistency, with an average particle size (Z average) of 290 nm (Zetasizer 4, Malvern Instruments, UK). At a high Galactolipids content (more than 5%) a thick paste is formed.

Emulsion B

| Ingredients | wt % |
| --- | --- |
| Water | 50.5 |
| Fractionated palm oil | 47.0 |
| Fractionated oat oil | 2.5 |

The palm oil is melted at 50° C. and mixed with the fractionated oat oil. The oil phase and the water are preheated to 65-70° C. and then the oil phase is added to the water under high-shear mixing at 15,000 rpm for 2 min. The pre-emulsion is then homogenised at 600 bar, for 5 cycles at 60° C. (Rannie homgenizer, Model Mini-Lab 8.30 H, APV Rannie, Denmark). This results in an emulsion with a cream-like consistency. The average particle size (Z average) is 400 nm (Zetasizer 4, Malvern Instruments, UK).

Example 3

Food Compositions

Ice Cream

Ingredients 2 eggs 125 mL sugar 250 mL milk 5 g orange-cocoa aroma 200 mL Olibra Eggs, sugar and milk are mixed and slowly boiled whilst whipping until the cream thickens. Then the cream is mixed with about 5 g orange-cocoa aroma (from NorrMejerier, Luleå, Sweden) and cooled to room temperature. 200 mL Olibra is added and the mixture is the poured into an ice cream machine and run for about 30 minutes.

Carrot Cake

Ingredients 4 eggs 250 mL Fractionated palm oil+Fractionated oat oil 600 mL grated carrot 200 mL brown sugar 150 mL sugar 1 teaspoon baking soda 1 teaspoon salt 3 teaspoons cinnamon 450 mL wheat flour The eggs and the mixture (40:2 by weight) of Fractionated palm oil and Fractionated oat oil are added to the grated carrots and the mixture obtained is whipped by an electric mixer. All the dry ingredients are mixed and gently stirred into the carrot mixture. The batter is poured into a high, oiled and breaded baking-tin and heated for 60 minutes at an oven temperature of 175° C.

Example 4

Study on Weight Maintenance after a Period of Weight Loss

Study Design

A randomized placebo-controlled, double-blind, parallel design was used. The design is schematically depicted in FIG. 1.

For the first 8 weeks of the study, 96 subjects (stratified for age, body mass index (BMI), body weight and dietary restraint) were at random divided into two groups of 48 subjects. Weight loss was achieved by a 6 weeks regimen of Modifast (2.1 MJ/d), used according to the instructions of the manufacturer; then a 18 weeks period of weight regain started where subjects resumed their habitual eating patterns and obtained either control or Olibra yogurt for daily use. One group received placebo yogurt (250 g yogurt with 5 g milkfat) and the other Olibra yogurt (250 g yogurt with 3 g milkfat and 2 g vegetable fat, provided by 5 g Olibra emulsion). Subjects were instructed to use 2 portions of 125 g in the morning (breakfast time) and 2 portions in the afternoon (around 16.00 hrs).

For the test day in week 1 (before weight loss), week 7 (after weight loss) and week 25 (after weight regain/maintenance), the same yogurts were used, but only 2 portions of 125 g were provided as breakfast.

Measurements that took place on the various test days are described below in the section Manufacturing of Olibra Yogurt All containers were warmed up to room temperature. About 4000 L of milk with a fat content of 2.2%, holding a temperature of 12° C., was mixed with about 150 L of Olibra with a fat content of 42%. The mixture was slowly stirred for 1 hour. Water and the other ingredients (sugar, whey powder, starch, skim milk powder and gelatine) were added to give a final fat content in the yogurt of 2.05% (including also the fruit preparation added later in the process).

The mixture was heated to 50° C. at pH 6.6-6.8 and then homogenised using a two-step high pressure homogeniser (190 bar/70 bar). The homogenised emulsion was pasteurised at about 90° C. for 5 min, followed by heat sterilisation at 120° C. After cooling to about 43° C., the resulting emulsion was incubated in a fermentation tank at pH 3.95-4.20 for about 8 h. The fermented product was then cooled and stored in a tank. The required amount of fruit preparation was added and additional heating of the yogurt to about 78° C. was performed. Finally, the yogurt was cooled and filled in 200 g plastic cups with Al seals and refrigerated until use.

Subjects

The subjects, recruited via a local newspaper, were 96 female overweight subjects, aged between 18 and 55 years and with a BMI between 25 and 30 kg/m$^2$. They were in good health, non-smokers, normotensive, not using medication and at most moderate alcohol users. We included only women due to differences between men and women, for example metabolic differences. Furthermore, there are indications that the effect of Olibra may be more pronounced in women than in men (Burns et al, 2000).

During screening body weight, height, waist-hip circumference and blood pressure were measured. A questionnaire on health, use of medication, smoking behaviour, alcohol consumption and physical activity was completed.

Measurements

Questionnaires (in Weeks 1, 7, 25)

The following questionnaires were used to measure (in the fasted state)

eating behavior (Three-Factor Eating Questionnaire, Stunkard & Messick, 1985)

hunger and satiety (Visual Analogue Scales)

mood (indicating the strength of all types of positive and negative moods like relaxed, gloomy, pleasant, angry, afraid, sad; Kovacs et al, 2003)

tolerance (possible side-effects of the treatment)

Blood Parameters (in Weeks 1, 7, 25)

The following blood parameters were measured in the fasted state: triacylglycerol (TG), free fatty acids (FFA) and glycerol (Gly) as indicators of lipolysis, and β-hydroxybutyrate (BHB) as indicator of fat oxidation. Altogether, 46 mL blood was taken in week 1, 7 and 25 (for satiety related hormones, TG, FFA, Gly and BHB measurements).

Anthropometry (in Week 2, 8, 26).

Body weight, waist-hip circumference and body composition were measured in the fasted state. Body composition was measured using the deuterium ($^2H_2O$) dilution technique. The dilution of the deuterium isotope is a measure for total body water (TBW). In the evening, the subjects ingested a dose of deuterium-enriched water ($^2H_2O$) after collecting a background urine sample. After ingestion of the deuterium solution no further fluid or food consumption was permitted. The following morning, the second urine sample (second voiding) was collected. Deuterium concentration in the urine samples was measured using an isotope ratio mass spectrometer (Micromass Optima, Manchester, UK). TBW was obtained by dividing the measured deuterium dilution space by 1.04 to correct for exchange of the $^2H$ label with nonaqueous hydrogen of body solids. Fat free mass (FFM) was calculated by dividing the TBW by hydrating factor 0.73. By subtracting FFM from body weight, fat mass (FM) was obtained. FM expressed as a percentage of body weight gives percentage of body fat (Schoeller et al, 1980; van Marken Lichtenbelt et al, 1994; Westerterp et al, 1995).

Resting Energy Expenditure (REE) (in Week 2, 8, 26)

The following energy expenditure and substrate oxidation variables were measured: basal metabolic rate, fat and carbohydrate oxidation for 30 min. During 3 days before the measurements the subjects consumed a standardized energy balance diet (100% of predicted energy expenditure; CHO/Protein/Fat as 53/12/35 En %). All food was supplied to the subjects. At the test day the subjects were requested to arrive in the morning at the laboratory in a fasted state. Basal metabolic rate and substrate oxidation were measured by means of an open circuit ventilated hood system with subjects lying supine for 30 min (Adriaens et al, 2003). Gas analysis was performed by a paramagnetic oxygen analyser (omnical type 1155B, Crowborough Sussex, UK) and an infrared carbon dioxide analyser (omnical type 1520/1507). REE was calculated using Weir's formula (Weir et al, 1949). The respiratory quotient (RQ) was calculated as $CO_2$ produced/$O_2$ consumed.

Satiety, Satiety Hormones (in Weeks 1, 7, and 25)

The subjects arrived at 8.00 hrs in a fasted state at the laboratory. An intravenous catheter was inserted. After collection of the baseline blood sample (t=0 min), the subjects received either Olibra or placebo yogurt. Blood sampling was repeated after 90 and 180 min. The catheter was removed after the last blood sample had been taken. Ghrelin (Ghr), Glucagon Like Peptide-1 (GLP-1) and Cholecystokinine (CCK) were measured in the fasted state and after 90 and 180 min to determine short-term satiety effects.

Hunger and satiety were recorded hourly by Visual Analogue Scales (VASs) since the subjective measurement represents in a robust and reproducible way the condition of the subject in this respect (Raben et al, 1995).

The subjects were not allowed to eat during the morning except drinking coffee, tea or water.

N Sampling in Urine (in Week 26)

At week 26, urine was collected during 24 hrs to determine the N-content in order to calculate the protein content of the diet. 24-h urine was collected from the second voiding on the first day until the first voiding on the second day. Samples were collected in containers with 10 mL $H_2SO_4$ to prevent nitrogen loss through evaporation. Volume and nitrogen concentration was measured, the latter using a nitrogen analyser.

Protein intake was calculated from the 24 hrs nitrogen output according to the following formula:

$$\text{Protein intake } (g/d) = (N \text{ output in 24 hrs urine } (g/d) + 20\%) \times 6.25$$

Urine N output is a constant fraction (80%) of N intake (Bingham et al, 1985).

Results

A. SUBJECT CHARACTERISTICS AT BASELINE

Table 1 shows that the subjects were well stratified according to their relevant baseline characteristics (screening values). There were 3 dropouts during the first 8 weeks. Values are means±sd

TABLE 1

| Baseline characteristics | Olibra group n = 47 | Placebo group n = 46 |
|---|---|---|
| Age (years) | 41.1 ± 10.0 | 40.9 ± 9.4 |
| Weight (kg) | 80.1 ± 7.7 | 77.6 ± 8.1 |
| Height (cm) | 167.1 ± 7.2 | 164.7 ± 7.4 |
| BMI (kg/m$^2$) | 28.7 ± 2.1 | 28.6 ± 2.1 |
| Waist circumference (cm) | 89.7 ± 6.0 | 90.0 ± 7.4 |
| Hip circumference (cm) | 108.3 ± 5.5 | 108.0 ± 6.7 |
| Waist/Hip ratio | 0.83 ± 0.04 | 0.83 ± 0.05 |
| Systolic blood pressure (mmHg) | 134.0 ± 15.9 | 131.3 ± 18.1 |
| Diastolic blood pressure (mmHg) | 82.9 ± 10.7 | 84.1 ± 9.7 |
| Heart Rate (beats/min) | 77.2 ± 14.4 | 76.5 ± 15.5 |

B. SUBJECT CHARACTERISTICS AT BASELINE AND AFTER 6 WEEKS OF WEIGHT LOSS

Characteristics of the subjects at baseline and after 6 weeks of weight loss are shown in table 2 (anthropometric, eating behaviour, mood, plasma lipids) and table 3 (satiety related hormones). No group over time effects was seen, so the stratified groups were still completely matched.

As shown in table 2, there was a significant reduction in body weight before the start of the use of either Olibra or placebo (p<0.05). Apart from the decreased body weight, there were also reductions (p<0.05) in BMI (kg/m$^2$), waist (cm), hip (cm), FFM (kg and %), FM (kg and %) and RQ. The F1 and F2, F3 score of the TFEQ (Three Factor Eating Questionnaire) respectively increased and decreased significantly, p<0.05. FFA (µmol/l) was significantly increased after 6 weeks weight loss. Fasted blood values of BHB (µmol/l) and TG (µmol/l) respectively increased and decreased significantly, p<0.05.

As presented in table 3, there was a significant decrease in CCK values (t0 and t180) after the weight loss period. Furthermore, Ghrelin was significantly increased at time point 180 after weight loss.

TABLE 2

Subject characteristics (anthropometric, eating behaviour, mood, plasma lipids) at baseline and after 6 weeks of weight loss

| | Olibra group n = 47 | Placebo group n = 46 | Total group n = 93 |
|---|---|---|---|
| | Before weight loss | | |
| Weight (kg) | 79.4 ± 7.7 | 77.4 ± 8.2 | 78.4 ± 8.0 |
| BMI (kg/m$^2$) | 28.4 ± 2.1 | 28.5 ± 2.2 | 28.5 ± 2.1 |
| Waist (cm) | 89.9 ± 5.7 | 90.4 ± 7.2 | 90.1 ± 6.5 |
| Hip (cm) | 108.0 ± 5.2 | 107.7 ± 7.4 | 107.9 ± 6.3 |
| FFM (kg) | 48.6 ± 5.2 | 46.6 ± 4.7 | 47.6 ± 5.1 |
| FFM (%) | 61.4 ± 3.8 | 60.4 ± 4.9 | 60.9 ± 4.4 |
| FM (kg) | 30.7 ± 4.7 | 30.8 ± 5.8 | 30.7 ± 5.3 |
| FM (%) | 38.7 ± 3.8 | 39.6 ± 4.9 | 39.1 ± 4.4 |
| RQ | 0.84 ± 0.05 | 0.83 ± 0.04 | 0.83 ± 0.04 |

TABLE 2-continued

Subject characteristics (anthropometric, eating behaviour, mood, plasma lipids) at baseline and after 6 weeks of weight loss

| | Olibra group n = 47 | Placebo group n = 46 | Total group n = 93 |
|---|---|---|---|
| F1 (TFEQ) | 8.4 ± 4.3 | 8.1 ± 3.7 | 8.2 ± 4.0 |
| F2 (TFEQ) | 6.7 ± 2.8 | 6.7 ± 2.3 | 6.7 ± 2.5 |
| F3 (TFEQ) | 5.2 ± 2.8 | 5.6 ± 3.0 | 5.4 ± 2.9 |
| Tolerance | 12.2 ± 7.7 | 11.0 ± 9.0 | 11.5 ± 8.2 |
| FFA (µmol/L) | 460.7 ± 180.0 | 529.5 ± 172.8 | 496.0 ± 181.1 |
| BHB (µmol/L) | 266.7 ± 145.0 | 278.4 ± 106.5 | 273.3 ± 128.3 |
| TG (µmol/L) | 880.4 ± 417.6 | 1008 ± 551.9 | 950.4 ± 498.2 |
| Glycerol (µmol/L) | 107.8 ± 48.3 | 118.2 ± 44.6 | 113.3 ± 47.1 |
| | After weight loss | | |
| Weight (kg) | 73.8 ± 7.5 | 71.0 ± 7.6 | 72.4 ± 7.6* |
| BMI (kg/m$^2$) | 26.4 ± 1.9 | 26.2 ± 2.3 | 26.3 ± 2.1* |
| Waist (cm) | 85.3 ± 5.7 | 84.4 ± 6.5 | 84.8 ± 6.1* |
| Hip (cm) | 104.0 ± 5.9 | 102.3 ± 7.5 | 103.2 ± 6.7* |
| FFM (kg) | 47.7 ± 5.7 | 45.0 ± 4.1 | 46.2 ± 5.2* |
| FFM (%) | 64.8 ± 4.8 | 63.5 ± 5.5 | 64.1 ± 5.3* |
| FM (kg) | 26.0 ± 4.8 | 26.2 ± 5.9 | 26.1 ± 5.4* |
| FM (%) | 35.2 ± 4.8 | 36.5 ± 5.5 | 35.9 ± 5.3* |
| RQ | 0.81 ± 0.04 | 0.80 ± 0.03 | 0.81 ± 0.03* |
| F1 (TFEQ) | 10.7 ± 3.8 | 11.7 ± 4.0 | 11.2 ± 3.9* |
| F2 (TFEQ) | 6.0 ± 2.8 | 5.5 ± 2.5 | 5.7 ± 2.7* |
| F3 (TFEQ) | 4.2 ± 3.5 | 4.2 ± 3.3 | 4.2 ± 3.3* |
| Tolerance | 12.3 ± 8.1 | 11.6 ± 8.3 | 12.0 ± 8.2 |
| FFA (µmol/L) | 596.3 ± 232.7 | 602.5 ± 161.6 | 599.3 ± 201.2* |
| BHB (µmol/L) | 419.7 ± 403.3 | 375.8 ± 188.3 | 400.1 ± 317.3* |
| TG (µmol/L) | 709.6 ± 369.9 | 843.9 ± 424.7 | 775.0 ± 403.0* |
| Glycerol (µmol/L) | 103.6 ± 38.4 | 106.2 ± 36.8 | 105.2 ± 37.5 |

Legend to Table 2:
Values are expressed as mean ± sd
*p < 0.05 over time difference (ANOVA repeated measures)
FFM (fat free mass, kg and %),
FM (fat mass, kg and %),
RQ (respiratory quotient),
factors 1, 2 and 3 of the TFEQ (Three Factor Eating Questionnaire: F1 = dietary restraint, F2 = disinhibition, F3 = general hunger), tolerance scores,
FFA (free fatty acids, (µmol/l)),
BHB (β-hydroxybutyrate, (µmol/l)),
TG (triglycerides, (µmol/l)),
Glycerol (µmol/l)

TABLE 3

Satiety related hormones GLP-1 (glucagon-like peptide 1), CCK (Cholecystokinin) and Ghr (Ghrelin): values at baseline and after 6 weeks weight loss in the fasted state, and 90 and 180 minutes after yogurt consumption; values are means ± sd

| | Olibra group n = 47 | Placebo group n = 46 | Total group n = 93 |
|---|---|---|---|
| | Before weight loss | | |
| | GLP-1 (glucagons-like peptide 1, pmol/L) | | |
| t0 (fasted) | 6.7 ± 3.6 | 6.4 ± 5.6 | 6.6 ± 4.7 |
| t90 | 7.4 ± 5.1 | 6.6 ± 4.8 | 6.9 ± 4.9 |
| t180 | 7.2 ± 4.8 | 7.8 ± 6.1 | 7.4 ± 5.5 |
| | CCK (cholecystokinin, pmol/L) | | |
| t0 (fasted) | 0.31 ± 0.39 | 0.38 ± 0.57 | 0.34 ± 0.49 |
| t90 | 1.83 ± 1.23 | 1.86 ± 1.26 | 1.85 ± 1.27 |
| t180 | 0.60 ± 0.84 | 0.90 ± 1.02 | 0.77 ± 0.96 |
| | Ghr (Ghrelin active, pg/mL) | | |
| t0 (fasted) | 115.0 ± 52.4 | 111.5 ± 44.7 | 115.2 ± 48.8 |
| t90 | 64.0 ± 39.6 | 56.1 ± 28.4 | 61.0 ± 35.1 |
| t180 | 132.5 ± 65.7 | 116.5 ± 55.5 | 124.2 ± 61.5 |

TABLE 3-continued

Satiety related hormones GLP-1 (glucagon-like peptide 1), CCK (Cholecystokinin) and Ghr (Ghrelin): values at baseline and after 6 weeks weight loss in the fasted state, and 90 and 180 minutes after yogurt consumption; values are means ± sd

| Olibra group n = 47 | Placebo group n = 46 | Total group n = 93 |
|---|---|---|
| After weight loss | | |
| GLP-1 (glucagons-like peptide 1, pmol/L) | | |
| 7.4 ± 4.5 | 6.3 ± 4.9 | 6.9 ± 4.7 |
| 7.4 ± 4.7 | 7.3 ± 5.2 | 7.4 ± 5.0 |
| 7.4 ± 5.6 | 7.0 ± 4.8 | 7.3 ± 5.2 |
| CCK (cholecystokinin, pmol/L) | | |
| 0.20 ± 0.38 | 0.22 ± 0.39 | 0.22 ± 0.39* |
| 1.69 ± 1.11 | 1.91 ± 1.31 | 1.79 ± 1.23 |
| 0.49 ± 0.73 | 0.43 ± 0.61 | 0.45 ± 0.68* |
| Ghr (Ghrelin active, pg/mL) | | |
| 109.8 ± 89.3 | 104.5 ± 50.1 | 107.9 ± 75.6 |
| 60.8 ± 30.9 | 70.9 ± 68.1 | 66.1 ± 53.2 |
| 156.4 ± 71.2 | 148.7 ± 79.3 | 153.4 ± 75.5* |

*$p < 0.05$ over time difference (ANOVA repeated measures)

C. WEIGHT MAINTENANCE PERIOD

The theoretical weight loss on a Modifast VLCD may be in the order of 11 kg over a 6 weeks period. Empirically, the typical weight loss amounts to about 1 kg per week. Part of this difference is due to non-compliance, part of it may be due to volunteers being allowed to eat low calorie fruits and vegetables whenever adherence to the strict VLCD is too difficult on a daily basis.

Thus, for the analysis of the results concerning consumption of either Olibra or placebo yogurt during the weight maintenance/regain period, only subjects who lost more than 6 kg during the Modifast VLCD weight loss period were included. This subgroup of 50 subjects is still matched for the baseline characteristics (table 4, week 1/2 and 7/8); the Olibra and placebo group lost 7.76±1.5 kg and 7.65±1.4 kg respectively.

C.1 Body Weight Maintenance during 18 Weeks

Figure 2:
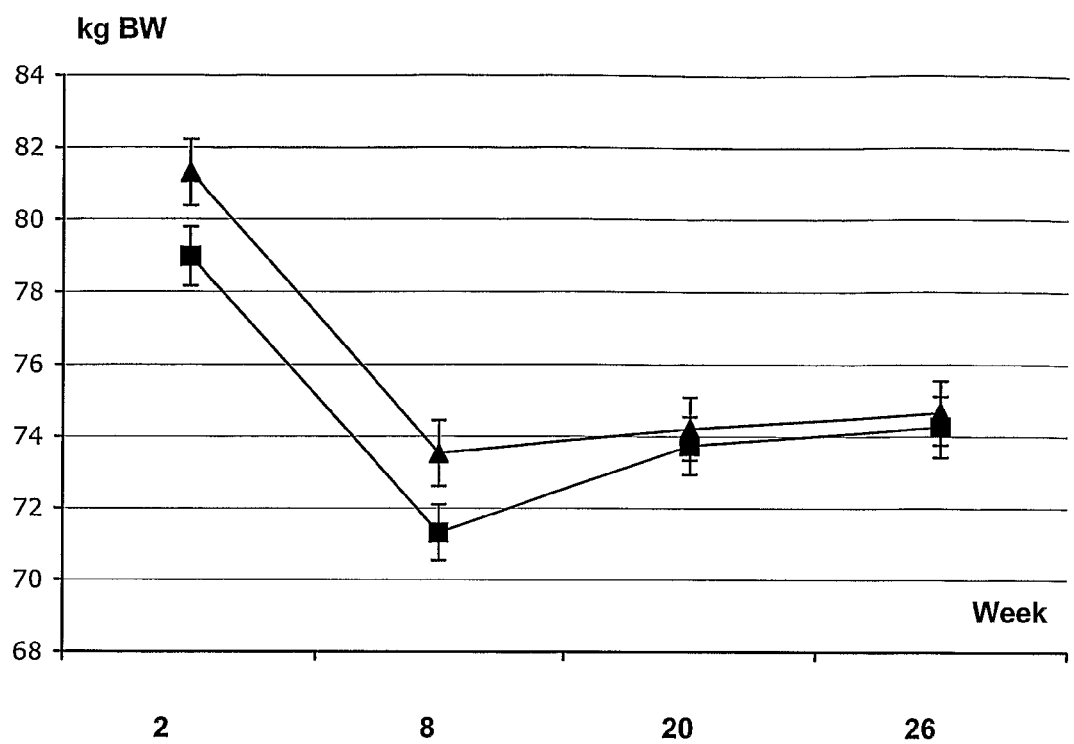
FIG. 2 shows the changes in body weight of the two groups in the study. Triangles is the weight of the Olibra group, squares is the weight of the control (placebo) group.
Figure 3:
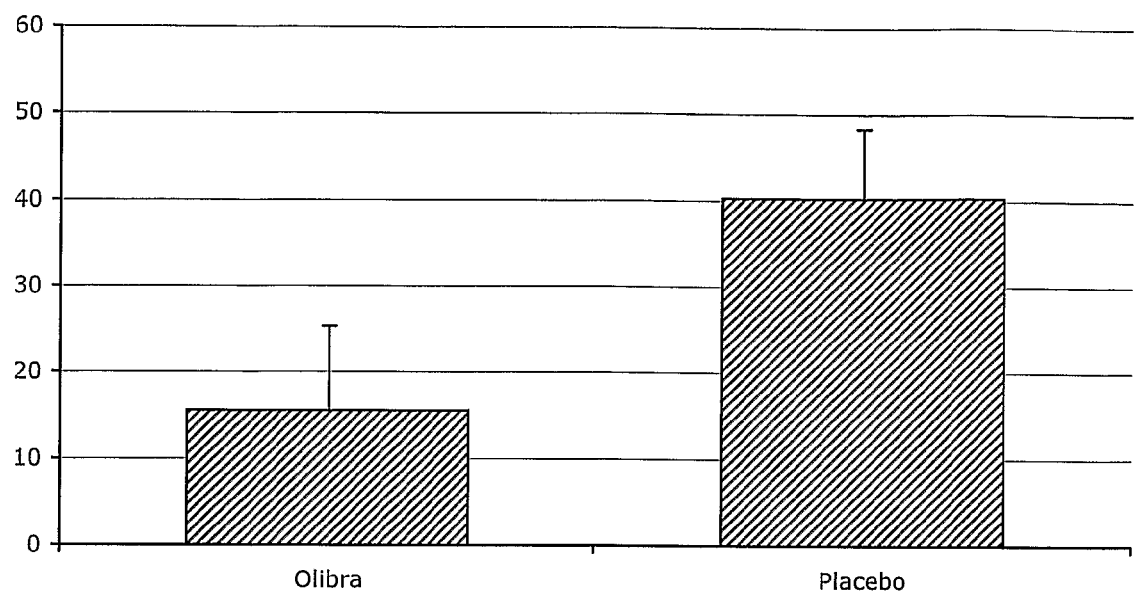
FIG. 3 shows the percentage weight regain after 26 weeks in the test, i.e. 18 weeks after a period of weight loss induced by a diet.

FIG. 2 and 3 and Table 4 (week 25/26) show the changes in body weight (BW) during the 18 weeks following weight loss. There was no significant increase in BW (kg) in the Olibra group (▲), whereas the placebo group (■) showed a significant increase in BW ($p<0.001$) (FIG. 2). A one-tailed, unpaired t-test showed a significant difference ($p<0.03$) in weight regain (kg and %) between both groups. Regain as % of weight loss was significantly lower with Olibra (15%) as compared to placebo yogurt (40%) (FIG. 3).

C.2 Changes in Anthropometric and Biochemical Characteristics (Table 4)

BMI (kg/m$^2$) and waist circumference (cm) did not increase in the Olibra group, but significantly increased in the placebo group ($p<0.05$). For waist circumference (cm), a treatment over time effect was seen during weight maintenance ($p<0.05$). Fat free mass (FFM; kg) significantly increased in both groups during weight maintenance. A treatment over time effect (week 26 compared to week 2) was seen for FFM (%) and FM compared to the placebo group ($p<0.05$). Fasted values of free fatty acids (FFA; μmol/l) and β-hydroxybutyrate (BHB; μmol/l) decreased in both groups, and triglycerides (TG; μmol/l) increased in both groups during weight maintenance ($p<0.05$).

TABLE 4

Subject characteristics at baseline and before and after weight maintenance (subjects who lost more than 6 kg of BW after 6 weeks of Modifast VLCD)

| | Olibra group n = 22 | Placebo group n = 28 |
|---|---|---|
| Week 1/2 | | |
| Weight (kg) | 81.3 ± 8.6 | 79.0 ± 8.6 |
| BMI (kg/m$^2$) | 28.9 ± 1.7 | 28.5 ± 2.2 |
| Waist (cm) | 91.1 ± 5.6 | 91.5 ± 7.7 |
| Hip (cm) | 108.8 ± 4.3 | 108.1 ± 7.1 |
| FFM (kg) | 50.0 ± 5.9 | 48.3 ± 4.5 |
| FFM (%) | 61.6 ± 3.9 | 61.8 ± 4.7 |
| FM (kg) | 31.3 ± 5.0 | 30.2 ± 6.2 |
| FM (%) | 38.4 ± 3.9 | 38.2 ± 4.7 |
| RQ | 0.83 ± 0.05 | 0.82 ± 0.04 |
| F1 (TFEQ) | 8.5 ± 4.3 | 7.9 ± 3.6 |
| F2 (TFEQ) | 7.2 ± 2.7 | 7.0 ± 2.1 |
| F3 (TFEQ) | 4.6 ± 3.0 | 5.4 ± 2.8 |
| Tolerance | 12.7 ± 6.9 | 11.3 ± 8.3 |
| FFA (μmol/L) | 437.3 ± 178.7 | 514.1 ± 159.0 |
| BHB (μmol/L) | 246.7 ± 135.0 | 281.5 ± 122.4 |
| TG (μmol/L) | 916.8 ± 500.0 | 1003.1 ± 599 |
| glycerol (μmol/L) | 97.3 ± 44.7 | 110.1 ± 41.8 |
| Week 7/8 | | |
| Weight (kg) | 73.5 ± 8.6 | 71.3 ± 8.3 |
| BMI (kg/m$^2$) | 26.1 ± 1.5 | 25.8 ± 2.2 |
| Waist (cm) | 83.9 ± 5.9 | 83.8 ± 6.9 |
| Hip (cm) | 103.0 ± 5.5 | 102.1 ± 6.8 |
| FFM (kg) | 48.3 ± 6.4 | 46.1 ± 4.1 |
| FFM (%) | 65.8 ± 4.6 | 65.0 ± 5.6 |
| FM (kg) | 25.2 ± 4.8 | 25.3 ± 6.3 |
| FM (%) | 34.2 ± 4.6 | 35.0 ± 5.6 |
| RQ | 0.79 ± 0.04 | 0.80 ± 0.03 |
| F1 (TFEQ) | 10.9 ± 3.8 | 11.6 ± 4.4 |
| F2 (TFEQ) | 6.1 ± 2.8 | 5.7 ± 2.3 |
| F3 (TFEQ) | 3.9 ± 3.7 | 3.6 ± 2.8 |
| Tolerance | 13.6 ± 7.9 | 12.3 ± 9.0 |
| FFA (μmol/L) | 677.4 ± 246.4 | 635.3 ± 168.5 |
| BHB (μmol/L) | 573.0 ± 525.3 | 417.1 ± 211.0 |
| TG (μmol/L) | 636.1 ± 263.3 | 774.4 ± 414.5 |
| glycerol (μmol/L) | 110.6 ± 43.8 | 107.7 ± 35.8 |
| Week 25/26 | | |
| Weight (kg) | 74.7 ± 8.3 | 74.3 ± 9.0* |
| BMI (kg/m$^2$) | 26.5 ± 1.9 | 26.9 ± 2.6* |
| Waist (cm) | 83.6 ± 5.0[1] | 85.5 ± 7.0* |
| Hip (cm) | 102.1 ± 7.3 | 102.9 ± 8.5 |
| FFM (kg) | 49.9 ± 6.0* | 48.1 ± 4.6* |
| FFM (%) | 66.9 ± 4.7[2] | 65.2 ± 6.1 |
| FM (kg) | 24.8 ± 5.0[2] | 26.1 ± 7.0 |
| FM (%) | 33.1 ± 4.7[2] | 34.8 ± 6.1 |
| RQ | 0.86 ± 0.05* | 0.84 ± 0.05* |
| F1 (TFEQ) | 11.6 ± 4.3 | 11.5 ± 3.7 |
| F2 (TFEQ) | 6.1 ± 2.6 | 6.0 ± 2.1 |
| F3 (TFEQ) | 4.1 ± 3.7 | 3.3 ± 2.7 |
| Tolerance | 12.0 ± 6.5 | 10.8 ± 7.4 |
| FFA (μmol/L) | 348.1 ± 116.1* | 439.1 ± 125.7* |
| BHB (μmol/L) | 275.0 ± 73.0* | 303.3 ± 111.4* |

TABLE 4-continued

Subject characteristics at baseline and before and after weight maintenance (subjects who lost more than 6 kg of BW after 6 weeks of Modifast VLCD)

|  | Olibra group n = 22 | Placebo group n = 28 |
|---|---|---|
| TG (µmol/L) | 792.9 ± 327.2* | 947.8 ± 508.3* |
| glycerol (µmol/L) | 109.0 ± 53.4 | 115.3 ± 40.1 |

Legend to Table 4
Values are means ± sd
*$p < 0.05$ over time difference compared to week 7/8 (ANOVA repeated measures)
[1]$p < 0.05$ treatment over time difference compared to week 7/8 (ANOVA repeated measures)
[2]$p < 0.05$ treatment over time difference compared to week 1/2 (ANOVA repeated measures)
BMI (Body Mass Index, kg/m$^2$), waist circumference (cm), hip circumference (cm),
FFM (fat free mass, kg and %),
FM (fat mass, kg and %),
RQ (respiratory quotient),
factors 1, 2 and 3 of the TFEQ (Three Factor Eating Questionnaire: F1 = dietary restraint, F2 = disinhibition, F3 = general hunger),
tolerance scores,
FFA (free fatty acids, µmol/L),
BHB (β-hydroxybutyrate, µmol/L),
TG (triglycerides, µmol/L)

C.3 Changes in Resting Energy Expenditure

Figure 4:
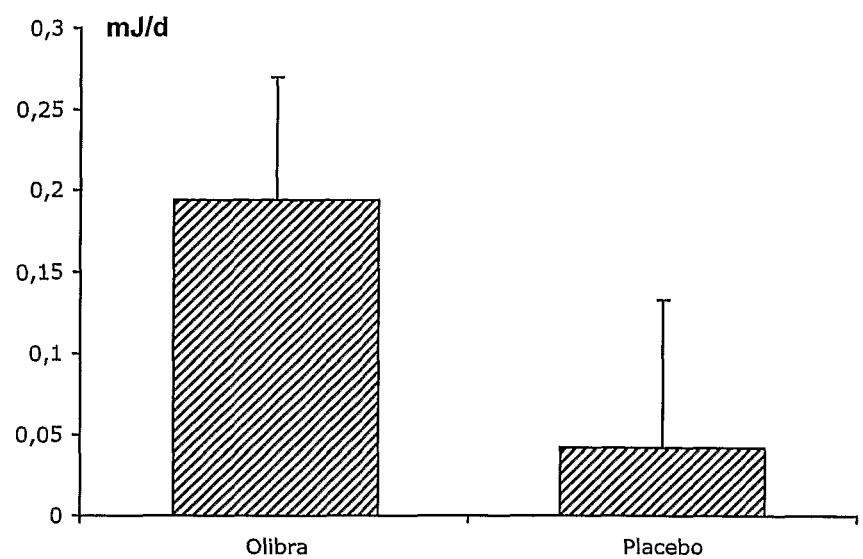
FIG. 4 shows a comparison of the REE in the two groups.

There was a significant linear relation between Resting Energy Expenditure (REE; mJ/d) and FFM (kg) in week 2 and 26 in both groups. To determine for each group whether changes in REE took place over time as a function of FFM (REE regressed against FFM), FFM (kg) of week 26 was filled in the slope equation of week 2. ANOVA repeated measures showed that the measured REE in week 26 was significantly higher ($p<0.05$) than the predicted REE in week 26 for the Olibra group but not for the placebo group (FIG. 4). A comparison of the differences between the predicted and measured REE in week 26 between both groups did not reach a significantly different treatment over time effect.

Figure 6:
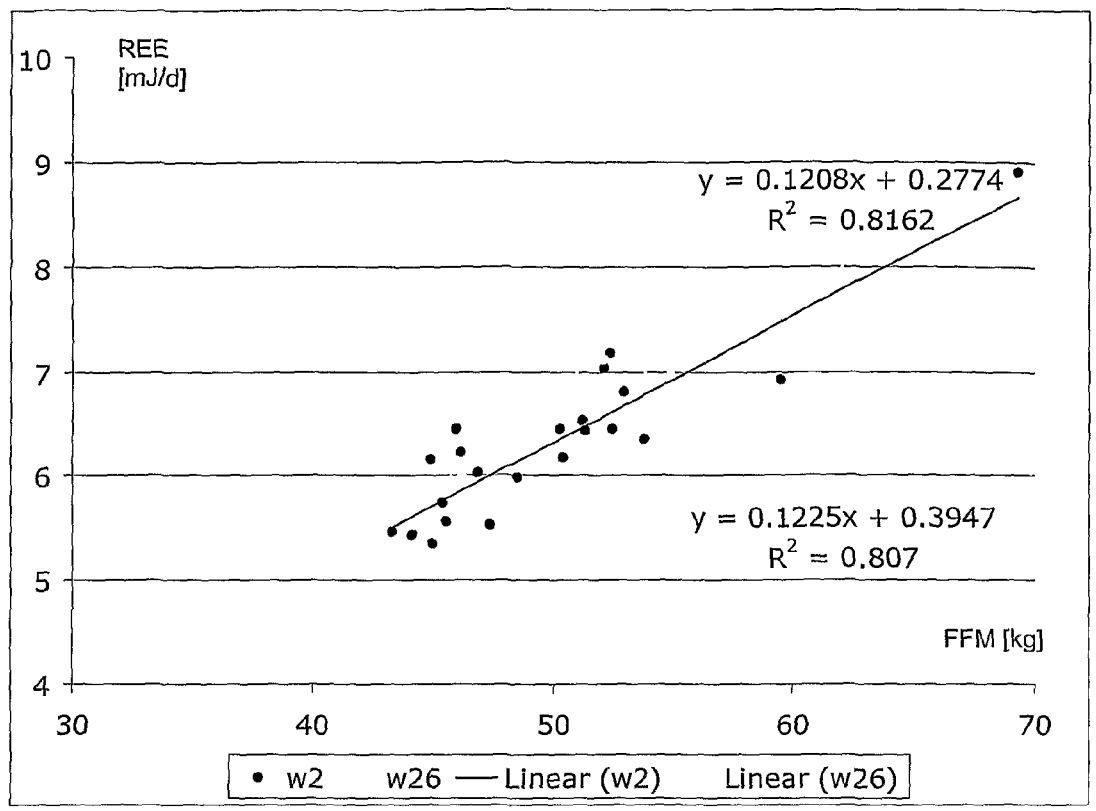
FIG. 6 shows a graph wherein REE is plotted against FFM for the Olibra group
Figure 7:
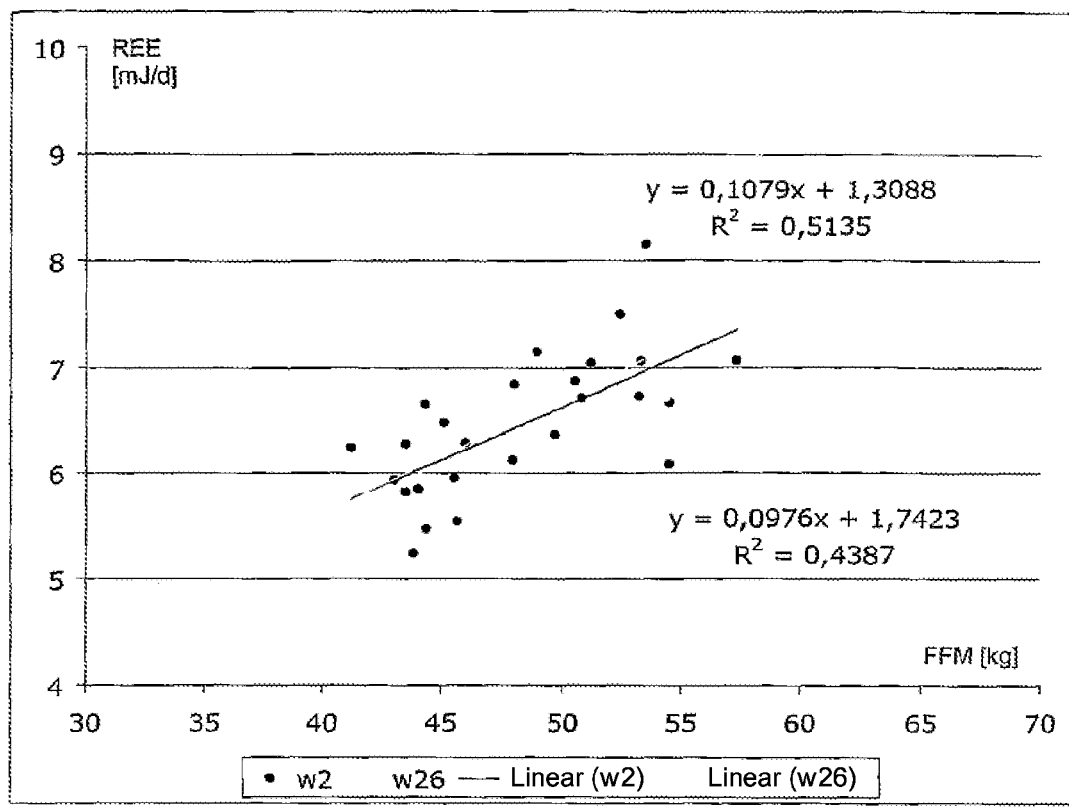
FIG. 7 shows a graph wherein REE is plotted against FFM for the control group

Table 5 provides the measured Resting Energy Expenditure of both groups in week 2 and week 26 together with the FFM data. FIGS. 6 and 7 show graphs wherein REE is plotted against FFM. It appears that there is a linear relationship between REE and FFM in both groups. It can be seen from table 5 that in the Olibra group there are 14/22 (64%) individuals that have a higher REE in week 26 as compared to week 2. In the control group, only 12/26 (46%) of the individuals had a higher REE in week 26 as compared to week 2.

TABLE 5

| | REE week 2 (mJ/d) | FFM week 2 (kg) | REE week 26 (mJ/d) | FFM week 26 (kg) |
|---|---|---|---|---|
| Olibra | 5.55 | 45.61 | 5.849 | 46.12 |
| | 5.972 | 48.53 | 5.944 | 48.21 |
| | 5.731 | 45.46 | 6.369 | 45.51 |
| | 6.423 | 51.35 | 7.111 | 52.15 |
| | 6.915 | 59.5 | 7.456 | 58.66 |
| | 6.447 | 52.51 | 7.004 | 54.99 |
| | 5.421 | 44.18 | 5.365 | 42.65 |
| | 5.454 | 43.33 | 5.742 | 42.96 |
| | 7.019 | 52.17 | 7.344 | 52.99 |
| | 6.447 | 46.03 | 6.166 | 43.29 |
| | 6.519 | 51.21 | 7.032 | 50.99 |
| | 6.152 | 44.96 | 5.568 | 43.08 |
| | 7.166 | 52.42 | 7.533 | 53.03 |
| | 6.799 | 53 | 6.317 | 49.24 |
| | 6.222 | 46.23 | 5.907 | 46.39 |
| | 6.438 | 50.29 | 6.553 | 54.37 |
| | 5.52 | 47.4 | 5.974 | 47.47 |
| | 6.16 | 50.48 | 6.514 | 48.32 |
| | 6.026 | 46.97 | 5.992 | 46.34 |

TABLE 5-continued

| | REE week 2 (mJ/d) | FFM week 2 (kg) | REE week 26 (mJ/d) | FFM week 26 (kg) |
|---|---|---|---|---|
| | 5.335 | 45.05 | 5.86 | 46.72 |
| | 8.902 | 69.31 | 8.815 | 66.04 |
| | 6.338 | 53.8 | 6.773 | 58.3 |
| Mean | 6.316 | 49.990 | 6.509 | 49.901 |
| Control | 5.845 | 44.01 | 5.569 | 42.67 |
| | 6.642 | 44.33 | 6.492 | 40.98 |
| | 6.712 | 53.28 | 6.486 | 51.13 |
| | 5.953 | 45.49 | 5.747 | 45.55 |
| | 7.487 | 52.46 | 7.361 | 55.95 |
| | 6.47 | 45.11 | 6.273 | 46.79 |
| | 7.056 | 57.36 | 7.151 | 55.11 |
| | 5.812 | 43.49 | 6.029 | 44.13 |
| | 6.071 | 54.57 | 6.355 | 48.4 |
| | 6.116 | 47.92 | 5.642 | 44.91 |
| | 8.136 | 53.56 | 8.109 | 52.4 |
| | 6.706 | 50.81 | 6.648 | 46.71 |
| | | | 7.362 | 55.44 |
| | 5.474 | 44.37 | 5.672 | 44.23 |
| | 6.66 | 54.52 | 6.43 | 52.58 |
| | 6.284 | 45.99 | 5.843 | 48.51 |
| | 6.233 | 41.19 | 6.341 | 40.88 |
| | 7.053 | 53.37 | 7.233 | 53.2 |
| | | | 6.696 | 54.4 |
| | 7.037 | 51.27 | 7.413 | 51.82 |
| | 5.232 | 43.85 | 5.723 | 44.28 |
| | 6.855 | 50.56 | 7.054 | 48.06 |
| | 7.135 | 48.98 | 7.695 | 51.74 |
| | 6.826 | 47.98 | 6.458 | 48.28 |
| | 6.353 | 49.7 | 5.867 | 48.12 |
| | 5.934 | 43.02 | 6.373 | 44.23 |
| | 6.262 | 43.5 | 5.917 | 42.01 |
| | 5.536 | 45.64 | 6.079 | 44.96 |
| Mean | 6.457 | 48.320 | 6.460 | 48.12 |

C.4 Hunger Ratings at Baseline and Before and After Weight Maintenance

Figure 5:
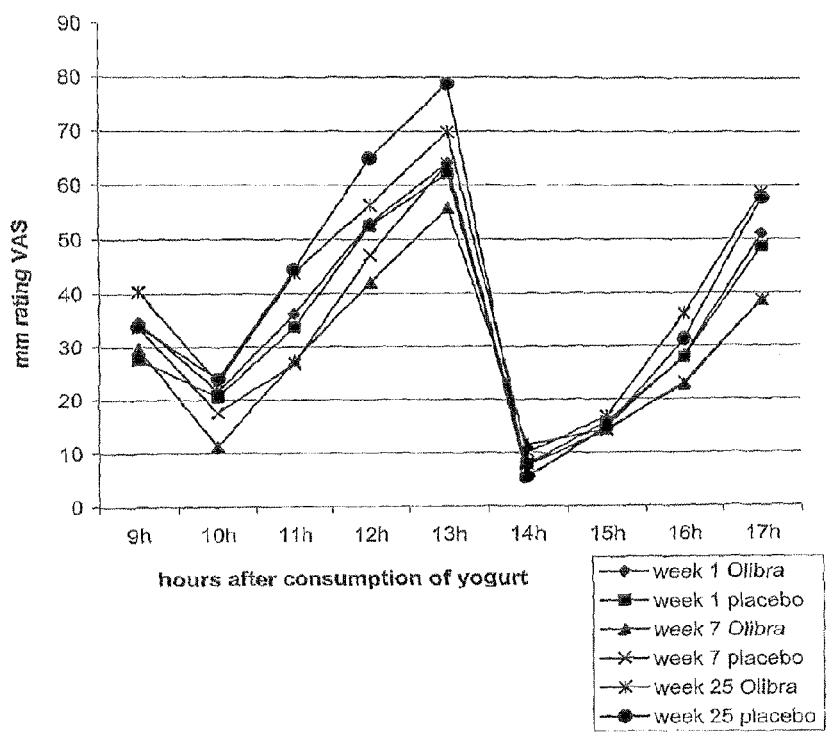
FIG. 5 shows the hunger scores in the two groups.

Hunger ratings at baseline and before and after weight maintenance are presented in FIG. 5 and table 6 for the morning and afternoon separately. Using the formula "hunger after breakfast=hunger (10 h–9 h)+hunger (13 h–10 h)", a significant difference was found between the Olibra group and the placebo group in week 25, in that the Olibra group was less hungry 4 h after yogurt consumption.

C.5 Satiety Related Hormones at the End of the Weight Management Period

Table 7 presents the levels of the satiety related hormones GLP-1, CCK, and Ghrelin before and after weight loss, and after weight maintenance. GLP-1 values at 180 minutes after yogurt consumption were significantly increased in week 25 compared to week 1 in the Olibra group (treatment over time effect, $p<0.05$). No other significant changes were noted between groups.

TABLE 6

Hunger scores at baseline and before and after weight maintenance

| | (10 h-9 h) + (13 h-10 h) | | 17 h-14 h | |
|---|---|---|---|---|
| | Olibra n = 22 | Placebo n = 28 | Olibra n = 22 | Placebo n = 28 |
| Week 1 | 29.4 ± 24.9 | 34.5 ± 33.2 | 45.7 ± 19.7 | 40.9 ± 23.5 |
| Week 7 | 26.1 ± 24.5 | 30.3 ± 22.3 | 27.2 ± 25.2 | 30.8 ± 21.8 |
| Week 25 | 29.4 ± 21.8 | 45.6 ± 30.0* | 48.8 ± 26.4 | 52.3 ± 22.0 |

Values are means ± sd.
9 h (hunger score before yogurt), 10 h (hunger score 1 hour after yogurt consumption), 13 h (hunger score before lunch), 14 h (hunger score 1 hour after lunch), 17 h (hunger score 4 hours after lunch)
*$p < 0.05$ AUC Hunger (10 h-9 h) + (13 h-10 h) (Olibra compared to placebo), factorial ANOVA

TABLE 7

GLP-1, CCK, and Ghrelin values in the fasted state, and after yogurt consumption, at baseline (week 1), after VLCD (week 7) and after the end of the weight maintenance period (week 25)

| | Week 1 | |
|---|---|---|
| | Olibra n = 22 | Placebo n = 28 |
| GLP-1 (glucagon-like peptide 1, pmol/L) | | |
| t0 (fasted) | 6.8 ± 3.6 | 6.2 ± 6.9 |
| t90 | 7.9 ± 6.5 | 6.7 ± 5.9 |
| t180 | 7.3 ± 5.8 | 7.8 ± 7.6 |
| CCK (cholecystokinin, pmol/L) | | |
| t0 (fasted) | 0.28 ± 0.35 | 0.38 ± 0.56 |
| t90 | 1.57 ± 1.12 | 1.74 ± 1.12 |
| t180 | 0.40 ± 0.56 | 0.72 ± 0.84 |
| Ghr (Ghrelin active, pg/mL) | | |
| t0 (fasted) | 120.7 ± 63.9 | 124.8 ± 49.5 |
| t90 | 62.1 ± 34.0 | 63.5 ± 33.3 |
| t180 | 142.9 ± 68.6 | 128.7 ± 60.4 |
| | Week 7 | |
| | Olibra n = 22 | Olibra n = 22 |
| GLP-1 (glucagon-like peptide 1, pmol/L) | | |
| t0 (fasted) | 7.5 ± 5.4 | 6.6 ± 5.9 |
| t90 | 7.8 ± 5.1 | 7.6 ± 6.5 |
| t180 | 7.4 ± 5.7 | 7.2 ± 5.7 |
| CCK (cholecystokinin, pmol/L) | | |
| t0 (fasted) | 0.15 ± 0.39 | 0.22 ± 0.41 |
| t90 | 1.55 ± 0.65 | 1.99 ± 1.25 |
| t180 | 0.33 ± 0.48 | 0.42 ± 0.56 |
| Ghr (Ghrelin active, pg/mL) | | |
| t0 (fasted) | 101.4 ± 57.9 | 105.4 ± 53.2 |
| t90 | 64.3 ± 37.1 | 83.3 ± 81.7 |
| t180 | 163.9 ± 61.7 | 168.9 ± 89.9 |
| | Week 25 | |
| | Placebo n = 28 | Olibra n = 22 |
| GLP-1 (glucagon-like peptide 1, pmol/L) | | |
| t0 (fasted) | 7.0 ± 6.7 | 6.3 ± 7.1 |
| t90 | 7.5 ± 6.8 | 7.3 ± 7.8 |
| t180 | 8.7 ± 6.1# | 7.5 ± 8.1 |
| CCK (cholecystokinin, pmol/L) | | |
| t0 (fasted) | 0.37 ± 0.50 | 0.48 ± 0.89 |
| t90 | 1.73 ± 0.93 | 2.34 ± 1.30 |
| t180 | 0.17 ± 0.22 | 0.58 ± 0.92 |
| Ghr (Ghrelin active, pg/mL) | | |
| t0 (fasted) | 162.5 ± 130.1 | 128.1 ± 41.5 |
| t90 | 124.2 ± 111.0 | 91.2 ± 28.9 |
| t180 | 132.2 ± 81.3 | 122.7 ± 54.5 |

Legend to Table 7
Values are means ± sd
$p < 0.05$ treatment over time compared to week 1 (ANOVA repeated measures)

C.6 Protein Consumption at the End of the Weight Maintenance Period

Table 8 shows that both groups had on average the same protein intake, i.e. 74.6±28.0 gram per day for the Olibra users and 81.8±31.0 gram per day for the placebo users; these intakes were not significantly different. Thus the yogurt results during weight maintenance were independent of the protein consumption during this period.

TABLE 8

Protein intake in yogurt groups at the end of the weight maintenance period

| | Olibra n = 22 | Placebo n = 28 |
|---|---|---|
| En % P | 12.8 ± 4.2 | 14.2 ± 5.0 |
| g P/24 h | 74.6 ± 28.0 | 81.8 ± 31.0 |

Values are means ± sd.
En % P (energy percentage protein in week 26); g P/24 h (gram of protein per 24 h in week 26, derived from the urinary nitrogen)

C.7 Possible Effects of Calcium on Body Weight or Composition

An inverse relation between calcium intake and body composition or body weight has been observed in a large variety of populations. A threshold of approximately 800 mg calcium per day above which calcium intake has no additional beneficial effect on body weight and body composition has been suggested from a number of studies (e.g. Zemel et al, 2003; Boon et al, 2005). In the Netherlands, calcium intake levels are already rather high (about 800-1600 mg per day); about 70% of the daily intake of calcium originates from dairy products (Hulshof et al, 2003). The daily calcium intake from the yogurt servings amounted to approximately 650 mg. Therefore, it is fair to assume that the daily intake of calcium during the study period was well above 800 mg per day, and that calcium effects on body weight or body composition are unlikely.

C.8 Human Study 12.5 g of Olibra (42%) was filled in 15 mL glass bottle with screw cap under controlled environmental conditions. The bottles were stored in refrigerator during the study but placed in room temperature 1-2 hours before use. The bag with meal replacement powder chocolate or forest berries was mixed with 200 mL water in a plastic container according to the instruction from the manufacturer and thereafter Olibra was poured into the container with the Nutrilett formulation and shaken for 5 seconds.

Sixteen overweight women with a BMI >26 kg/m² replaced all their meals with a VLCD diet for six weeks to lose weight. The VLCD diet consisted of five bags of Nutrilett Intensive with a total energy content of 2.3 kJ/day. After the weight loss period the subjects returned to their habitual eating patterns and replaced lunch with one bag of Nutrilett Intensive and 12.5 g Olibra was added to the meal replacement beverage. The subjects continued to replace lunch with the test product for 8 weeks but had no other restrictions for the rest of the day such as type or amount of food, Table 9.

TABLE 9

| No of Subjects | Baseline weight (kg) | Weight after 6 weeks (kg) | Weight after 14 weeks (kg) |
|---|---|---|---|
| 16 | 79.2 ± 5.8 | 71.9 ± 4.5 | 70.9 ± 4.5 |

Values are means ± sd

D. CONCLUSIONS

For the analysis of the long term effects of Olibra versus the milk fat placebo, 50 subjects who lost at least 6 kg weight during the weight loss period were included.

The following conclusions can be drawn from this 18 weeks field study:
1. the weight regain in the Olibra group was not significant, whereas in the placebo group it was; weight regain as % of weight loss was significantly lower with Olibra (15%) than with placebo yogurt (40%) (table 4 and FIGS. 2 and 3)
2. fat mass (FM; kg and %) decreased and fat free mass (FFM; %) increased with Olibra yogurt in week 26 compared to week 2 (before weight loss) (table 4)
3. the measured resting energy expenditure (REE; mJ/d) as a function of FFM in week 26 was significantly higher than the predicted REE in week 26 for Olibra consumption, but not for placebo consumption (FIG. 4)
4. hunger scores during 4 hours after morning consumption of Olibra yogurt were increased at the end of the weight regain period; yet, no significant differences were seen between yogurts during the test days in the laboratory at baseline or after weight loss
5. no significant changes were observed in satiety related hormones in the fasted state, or 90 or 180 minutes after yogurt consumption
6. calcium nor protein intake are likely to have influenced the results obtained with the two different yogurts The better weight maintenance upon consumption of Olibra yogurt compared to placebo can be explained by relatively higher REE as a function of FFM. This may also have contributed the relatively higher increase in FFM and decrease in FM.

E. REFERENCES

Adriaens M P E, Schoffelen P F M, Westerterp K R. Intra-individual variation of basal metabolic rate and the influence of daily habitual physical activity before testing. Br J Nutr 2003, 90, 419-423.

Aponte G W, Fink A S, Meyer J H, Tatemoto K, Taylor I L. Regional distribution and release of peptide YY with fatty acids of different chain length. Am J Physiol 1985, 249, G745-750.

Bingham A S, Cummings J H. Urine nitrogen as an independent validatory measure of dietary intake: a study of nitrogen balance in individuals consuming their normal diet. Am J Clin Nutr 1985, 42, 1276-1289.

Boon N, Koppes L L J, Saris W H M, Van Mechelen W. The relation between calcium intake and body composition in a Dutch population. The Amsterdam growth and health longitudinal study. Am J Epidemiol 2005, 162, 27-32.

Burns A A, Livingstone M B E, Welch R W, Dunne A, Robson P J, Lindmark L, Reid C A, Mullaney U, Rowland I R. Short term effects of yogurt containing a novel fat emulsion on energy and macronutrient intakes in non-obese subjects. Int J Obes 2000, 24, 1419-1425.

Burns A A, Livingstone M B E, Welch R W, Dunne A, Reid C A, Rowland I R. The effects of yogurt containing a novel fat emulsion on energy and macronutrient intakes in non-overweight, overweight and obese subjects. Int J Obes 2001, 25, 1487-1496.

Burns A A, Livingstone M B E, Welch R W, Dunne A, Rowland I R. Dose-response effects of a novel fat emulsion (Olibra™) on energy and macronutrient intakes up to 36 h post-consumption. Eur J Clin Nutr 2002, 56, 368-377.

Hulshof K F, Brussaard J H, Kruizinga A G, Telman J, Lowik M R. Socio-economic status, dietary intake and 10y trends: the Dutch National Food Consumption Survey. Eur J Clin Nutr 2003, 57, 128-137.

Jin H, Gai L, Lee K, Chang T M, Li P, Wagner D, Chey W Y. A physiological role of peptide YY on exocrine pancreatic secretion in rats. Gastroenterology 1993, 105, 208-215.

Kovacs E M, Lejeune M P, Westerterp-Plantenga M S. The effects of enterostatin intake on food intake and energy expenditure. Br J Nutr 2003, 90, 207-214.

Lejeune M P, Kovacs E M, Westerterp-Plantenga M S. Additional protein intake limits weight regain after weight loss in humans. Br J Nutr 2005, 93, 281-289.

Pasman W J, Westerterp-Plantenga M S, Waris W H M. The effectiveness of long-term supplementation of carbohydrate, chromium, fibre and caffeine on weight maintenance. Int J Obes 1997, 21, 1143-1151.

Raben A, Hoist J J, Christensen N J, Astrup A. Determinants of postprandial appetite sensations: macronutrient intake and glucose metabolism. Int J Obes 1995, 20, 161-169.

Schoeller D A, van Santen E, Peterson D W, Dietz W, Jaspan J, Klein P D. Total body water measurement in humans with 18O and 2H labeled water. Am J Clin Nutr 1980, 33, 2686-2693.

Spiller R C, Trotman I F, Higgens B E, Ghatel M A, Grimble G K, Lee Y C, Bloom S R, Misiewics J J, Silk D B A. The ileal brake-inhibition of jejunal motility after ileal fat perfusion in man. Gut 1984, 25, 365-374.

Van Marken Lichtenbelt W D, Westerterp K, Wouter L. Deuterium dilution as a method for determining total body water: effect of test protocol and sampling time. Br J Nutr 1994, 72, 491-497.

Weir J B D V. New methods for calculating metabolic rate with special references to protein metabolism. J Physiol 1949, 109, 1-9.

Westerterp K R, Wouters L, van Marken Lichtenbelt W D. The maastricht protocol for the measurement of body composition and energy expenditure with labeled water. Obes Res 1995, 3(suppl 1), 49-57.

Westerterp-Plantenga M S. The significance of protein in food intake and body weight regulation. Current opinion in Clinical Nutrition and Metabolic Care, 2003, 6, 635-639.

Westerterp-Plantenga M S, Lejeune M P, Nijs I, Van Ooijen M, Kovacs E M. High protein intake sustains weight maintenance after weight loss in humans. Int J Obes Relat Metab Disord 2004, 28, 57-64.

Zemel M B. Mechanisms of dairy modulation of adiposity. J Nutr 2003, 133, 252S-256S.

The invention claimed is:

1. A method of maintaining one's weight after a weight loss period comprising:
    ingesting a emulsion comprising (a) a fractionated oat oil (b) a triglyceride oil having a solid fat content at ambient to body temperature and (c) a galactolipid emulsifier for a period of time following the weight loss period; and
    observing weight maintance, wherein any weight regained is less than 35% of lost Body Mass Index points.

2. A method according to claim 1 wherein the weight loss period lasted for at least 6 weeks.

3. A method according to claim 1 wherein the amount of weight lost during the weight loss period was at least 2% of one's baseline body weight.

4. A method according to claim 1 wherein any weight regained occurs within 18 weeks after the end of the weight loss period.

5. A method according to claim 1 wherein the emulsion is consumed in a food composition.

* * * * *

UNITED STATES PATENT AND TRADEMARK OFFICE
CERTIFICATE OF CORRECTION

PATENT NO.       : 8,329,759 B2
APPLICATION NO.  : 12/158001
DATED            : December 11, 2012
INVENTOR(S)      : Steijns et al.

Page 1 of 1

It is certified that error appears in the above-identified patent and that said Letters Patent is hereby corrected as shown below:

On the Title page Item (22) should read as, PCT Filed: Dec. 19, 2006

Signed and Sealed this
Twenty-third Day of April, 2013

Teresa Stanek Rea
*Acting Director of the United States Patent and Trademark Office*